(12) United States Patent
Dronov

(10) Patent No.: US 9,162,068 B2
(45) Date of Patent: Oct. 20, 2015

(54) ENERGY EFFICIENT RESONANT DRIVING CIRCUIT FOR MAGNETICALLY COUPLED TELEMETRY

(75) Inventor: Vasily Dronov, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1664 days.

(21) Appl. No.: 11/780,369

(22) Filed: Jul. 19, 2007

(65) Prior Publication Data

US 2009/0024179 A1      Jan. 22, 2009

Related U.S. Application Data

(63) Continuation-in-part of application No. 11/778,486, filed on Jul. 16, 2007, now abandoned.

(51) Int. Cl.
| | | |
|---|---|---|
| *A61N 1/37* | (2006.01) | |
| *A61N 1/372* | (2006.01) | |
| *A61N 1/36* | (2006.01) | |

(52) U.S. Cl.
CPC ........ *A61N 1/37223* (2013.01); *A61N 1/36071* (2013.01)

(58) Field of Classification Search
USPC ................. 607/33, 60–65; 323/355, 358; 363/21.02; 320/108
See application file for complete search history.

(56) References Cited

U.S. PATENT DOCUMENTS

| | | | | |
|---|---|---|---|---|
| 3,357,434 A | * | 12/1967 | Abell ................................ 607/2 |
| 3,942,535 A | * | 3/1976 | Schulman ....................... 607/33 |
| 4,441,210 A | * | 4/1984 | Hochmair et al. ........... 455/41.1 |
| 4,561,443 A | | 12/1985 | Hogrefe et al. ......... 128/419 PG |
| 5,324,315 A | * | 6/1994 | Grevious ........................ 607/60 |
| 5,562,714 A | * | 10/1996 | Grevious ........................ 607/32 |
| 5,735,887 A | | 4/1998 | Barreras, Sr. et al. .......... 607/60 |

(Continued)

FOREIGN PATENT DOCUMENTS

| | | | |
|---|---|---|---|
| WO | 0128629 A1 | 4/2001 | |
| WO | 2004/002572 | 1/2004 | ............... A61N 1/36 |

(Continued)

OTHER PUBLICATIONS

International Preliminary Report on Patentability and Written Opinion in corresponding PCT application No. PCT/US2008/067151, dated Jan. 28, 2010.

(Continued)

*Primary Examiner* — Paula J Stice
(74) *Attorney, Agent, or Firm* — Lewis & Reese, PLLC

(57) ABSTRACT

A driving circuit useful in a magnetic inductive coupling wireless communication system is disclosed. The circuit includes an inductor (coil; L) and capacitor (C) in series selectively coupled to a power source such as a rechargeable battery. The LC circuit is made to resonate in accordance with a Frequency Shift Keying (FSK) or other protocol. Such resonance produces a voltage across the inductor. This voltage is used to create a first voltage either by tapping into the coil, or by providing a transformer. The first voltage is coupled to the rechargeable battery by a diode. When the circuit resonates, and when the first voltage exceeds the voltage of the power source, the diode turns on, thus shunting excess current back to recharge the rechargeable battery. By use of this circuit, energy is conserved. Additionally, oscillations can be quickly dampened so as to allow the circuit to transmit at high data rates.

6 Claims, 6 Drawing Sheets

(56) References Cited

U.S. PATENT DOCUMENTS

| | | | |
|---|---|---|---|
| 5,769,877 A | 6/1998 | Barreras, Sr. | 607/61 |
| 6,349,116 B1 | 2/2002 | Hash et al. | |
| 6,442,434 B1 * | 8/2002 | Zarinetchi et al. | 607/61 |
| 6,516,227 B1 | 2/2003 | Meadows et al. | 607/46 |
| 6,553,263 B1 | 4/2003 | Meadows et al. | 607/61 |
| 6,658,300 B2 * | 12/2003 | Govari et al. | 607/60 |
| 6,894,456 B2 | 5/2005 | Tsukamoto et al. | 320/107 |
| 6,937,894 B1 | 8/2005 | Isaac et al. | 607/5 |
| 7,151,914 B2 | 12/2006 | Brewer | 455/127.1 |
| 7,177,698 B2 | 2/2007 | Klosterman et al. | 607/60 |
| 2003/0040291 A1 | 2/2003 | Brewer | 455/127 |
| 2003/0085684 A1 | 5/2003 | Tsukamoto et al. | 320/108 |
| 2004/0039423 A1 | 2/2004 | Dolgin | |
| 2004/0059392 A1 | 3/2004 | Parramon et al. | 607/36 |
| 2005/0021108 A1 | 1/2005 | Klosterman et al. | 607/48 |
| 2005/0119716 A1 | 6/2005 | McClure et al. | 607/61 |
| 2005/0131494 A1 | 6/2005 | Park et al. | 607/60 |
| 2005/0131495 A1 | 6/2005 | Parramon et al. | 607/61 |
| 2007/0032839 A1 | 2/2007 | Parramon et al. | 607/60 |
| 2007/0055308 A1 | 3/2007 | Haller et al. | 607/2 |
| 2007/0129768 A1 | 6/2007 | He et al. | 607/34 |
| 2007/0135867 A1 | 6/2007 | Klosterman et al. | 607/60 |
| 2007/0150019 A1 | 6/2007 | Youker et al. | 607/29 |
| 2007/0293914 A1 | 12/2007 | Woods et al. | 607/60 |

FOREIGN PATENT DOCUMENTS

| | | | |
|---|---|---|---|
| WO | 2007/030496 | 3/2007 | A61N 1/378 |
| WO | 2007/067825 | 6/2007 | A61N 1/378 |

OTHER PUBLICATIONS

U.S. Appl. No. 11/778,486, filed Jul. 16, 2007, Dronov.

PCT Search report for international application No. PCT/US2008/067151 dated Oct. 24, 2008.

\* cited by examiner

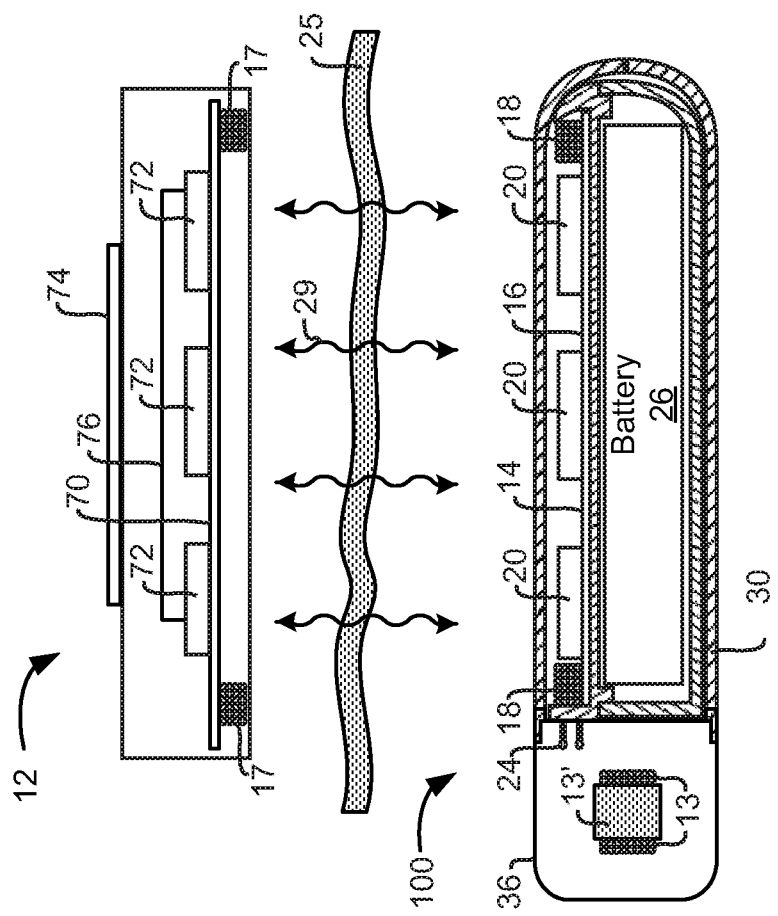

ENERGY EFFICIENT RESONANT DRIVING CIRCUIT FOR MAGNETICALLY COUPLED TELEMETRY

CROSS-REFERENCE TO RELATED APPLICATIONS

This is a continuation-in-part (CIP) application of U.S. patent application Ser. No. 11/778,486, filed Jul. 16, 2007, which is incorporated herein by reference and to which priority is hereby claimed.

FIELD OF THE INVENTION

The present invention relates to a driving circuit useable in a magnetically-coupled telemetry system, and has particular applicability to implantable medical device systems.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The present invention may find applicability in all such applications, although the description that follows will generally focus on the use of the invention within a Spinal Cord Stimulation (SCS) system, such as that disclosed in U.S. Pat. No. 6,516,227, which is incorporated herein by reference in its entirety.

Spinal cord stimulation is a well-accepted clinical method for reducing pain in certain populations of patients. As shown in FIGS. 1A and 1B, a SCS system typically includes an Implantable Pulse Generator (IPG) 100, which includes a biocompatible case 30 formed of titanium for example. The case 30 typically holds the circuitry and power source or battery necessary for the IPG to function, although IPGs can also be powered via external RF energy and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary.

As shown in FIG. 2, the IPG 100 typically includes an electronic substrate assembly 14 including a printed circuit board (PCB) 16, along with various electronic components 20, such as microprocessors, integrated circuits, and capacitors mounted to the PCB 16. Two coils are generally present in the IPG 100: a telemetry coil 13 used to transmit/receive data to/from an external controller 12 as explained further below; and a charging coil 18 for charging or recharging the IPG's power source or battery 26 using an external charger (not shown). The telemetry coil 13 can be mounted within the header connector 36 as shown.

As just noted, an external controller 12, such as a hand-held programmer or a clinician's programmer, is used to send data to and receive data from the IPG 100. For example, the external controller 12 can send programming data to the IPG 100 to dictate the therapy the IPG 100 will provide to the patient. Also, the external controller 12 can act as a receiver of data from the IPG 100, such as various data reporting on the IPG's status. The external controller 12, like the IPG 100, also contains a PCB 70 on which electronic components 72 are placed to control operation of the external controller 12. A user interface 74 similar to that used for a computer, cell phone, or other hand held electronic device, and including touchable buttons and a display for example, allows a patient or clinician to operate the external controller 12.

Wireless data transfer between the IPG 100 and the external controller 12 takes place via inductive coupling, and specifically magnetic inductive coupling. To implement such functionality, both the IPG 100 and the external controller 12 have coils 13 and 17 respectively. Either coil can act as the transmitter or the receiver, thus allowing for two-way communication between the two devices. When data is to be sent from the external controller 12 to the IPG 100 for example, coil 17 is energized with alternating current (AC), which induces an electromagnetic field 29, which in turn induces a current in the IPG's telemetry coil 13. The power used to energize the coil 17 can come from a battery 76, which like the IPG's battery 26 is preferably rechargeable, but power may also come from plugging the external controller 12 into a wall outlet plug (not shown), etc. The induced current in coil 13 can then be transformed at the IPG 100 back into the telemetered data signals. To improve the magnetic flux density, and hence the efficiency of the energy transfer, the IPG's telemetry coil 13 may be wrapped around a ferrite core 13'.

As is well known, inductive transmission of data from coil 17 to coil 13 can occur transcutaneously, i.e., through the patient's tissue 25, making it particular useful in a medical implantable device system. During the transmission of data, the coils 13 and 17 lie in planes that are preferably parallel. Such an orientation between the coils 13 and 17 will generally improve the coupling between them, but deviation from ideal orientations can still result in suitably reliable data transfer.

To communicate a serial stream of digital data bits via inductive coupling, some form of modulation is generally employed. In a preferred embodiment, Frequency Shift Keying (FSK) can be employed, in which the logic state of a bit (either a logic '0' or a logic '1') corresponds to the frequency of the induced magnetic field 29 at a given point in time. Typically, this field has a center frequency (e.g., fc=125 kHz), and logic '0' and '1' signals comprise offsets from that center frequency (e.g., f0=121 kHz and f1=129 kHz respectively). Once the data is modulated in this manner at the transmitting device (e.g., the external controller 12), it is then demodulated at the receiving device (e.g., the IPG 100) to recover the original data. While FSK modulation may be preferred for a given application, one skilled in the art will recognize that other forms of data modulation (e.g., amplitude modulation, On-Off-Keying (OOK), etc.) can be used as well. These modulation schemes as used in a medical implantable device system are disclosed in U.S. Pat. No. 7,177,698, which is incorporated herein by reference in its entirety, and because they are well known, they are not further discussed.

A typical driving circuit (or an amplifier circuit) 150 used to energize the transmitting coil is shown in FIG. 3. In the example shown it is assumed that the external controller 12 is acting as the transmitter, although it should be remembered that the IPG 100 could also act as the transmitter. The driving circuit 150 comprises a RLC circuit (or as it is sometimes known in the art, a "tank circuit" or "resonant circuit"), in which the inductor (L) comprises the coil 17 in the external controller discussed previously. As one skilled in the art understands, the RLC circuit is made to resonate by the application of a clock signal to switches 152 and 152'. Specifically, in the embodiment shown, switches 152 and 152' are toggled out of phase, which is accomplished using clocking signals, Clk and Clk', which are the inverse or complement of each other. The clock signals are derived from a modulation circuit 170, which converts the incoming data bit stream (Din) into clock signals with offset frequencies f0 and f1 indicative of the logic state of the bits. This induces a resonance in the RLC circuit, with the result that a magnetic field 29 is produced that wirelessly communicates the modulated data. In other words, a wireless modulated data signal 29 is produced.

The driving circuit 150 of FIG. 3 has advantages and disadvantages, particularly as relates to the use of the resistor R in the circuit. One advantage of using resistor R is that it results in a wider frequency response characteristic of the RLC circuit as shown to the right in FIG. 3. That is, the amplitudes of the two frequencies f1 and f0 as produced in magnetic field 29 are insensitive to small variations of f1 and f0. This property of the RLC circuit makes detection at the receiver side of the communication (e.g., at the IPG 100) simpler: in the case the receiver's tuning does not exactly match the frequencies (f0 and f1) of the transmitter, f0 and f1 values can be adjusted by the transmitter without affecting their amplitudes to a significant degree, thus improving the likelihood of successfully detecting the communicated signal. Additionally, the resistor helps to dampen the resonance of the resonant circuit. This is important to the data rate or "bandwidth" of the communication. If resonance at one frequency (e.g., f0) can be dampened relatively quickly, a next bit of the other frequency (e.g., f1) can be accurately produced that much more quickly, which in turn allows the data rate of the communication to increase.

However, the resistor R also produces a significant disadvantage, namely excessive power consumption. As one skilled in the art will appreciate, a resistor dissipates energy, and hence operation of the driving circuit 150 of FIG. 3 will need to consume more power by virtue of the passage of current through the resistor, R. In this regard, note that the driving circuit 150 is powered by the external controller 12's rechargeable battery 76. Because ease in use and portability suggests that the external controller 12 have an internal battery 76, it is appreciated that this battery 76 should preferably last as long as possible, thus saving the user from the inconvenience of frequently having to recharge the battery 76, or replace a non-rechargeable battery 76 with a fresh battery. Viewed from another perspective, excessive power consumption in the driving circuit 150 effectively limits the operable distance between the external control 12 and the IPG 100, given that power consumption and distance are proportional. To summarize, the driving circuit 150 illustrated in FIG. 3 can be said to have a low quality factor or "Q factor," because the ratio of the energy in the produced field 29 to the energy used to produce that field is relatively low.

FIG. 4 illustrates another prior art driving circuit 150', and particularly illustrates a simplified version of the approach disclosed in U.S. Pat. No. 6,349,116, which is hereby incorporated by reference in its entirety. In this circuit, a FSK modulated field 29 is also produced, but without the use of any significant resistances, R. Instead, a LC resonant circuit is formed by connecting the coil 17 and a base capacitor C0 in parallel. This basic resonant circuit is made to resonate via control of a switch 154 which is clocked at the higher offset frequency, f1. The data modulates the frequency of the produced oscillation by switching in another capacitor, C(fsk), via switch 156, again in parallel with L and C0. This has the effect of changing the resonant frequency to the lower offset frequency, f0, and thus by this arrangement, both frequencies f0 and f1 can be transmitted by either including or excluding the additional capacitance, C(fsk).

But just like the driving circuit of FIG. 3, driving circuit 150' too has its advantages and disadvantages. Advantageously, because the driving circuit 150' lacks a substantial resistance, the circuit is very energy efficient, and has a high Q factor. In other words, the driving circuit 150' does not overtax the battery 76, and thus allows for relatively long battery life and/or longer operating distances between the external controller 12 and the IPG 100.

However, disadvantageously, driving circuit 150' produces a wireless modulated data signal 29 with relatively narrow frequency response characteristic, as shown to the right in FIG. 4. As discussed above, this makes reception of the wireless data more difficult, and requires good matching between the transmitter and the receiver. In fact, the '116 patent specifically attempts to remediate this concern by providing a bank of additional tuning capacitors, C(1) through C(n). As shown in FIG. 4, these tuning capacitors C(1) through C(n) must be selectively switched in parallel with the base capacitor C0 using switches 158(1) through 158(n). This is regrettable, because this requires additional overhead and circuitry necessary to assess the produced frequencies and to tune them accordingly. Such added complexity makes driving circuit 150' a poor choice for utilization in portable devices, and even more so for the case of implantable devices.

From the foregoing, it should be clear that the art of magnetically-coupled telemetry systems would benefit from a new driving circuit, one which: produces a relatively wide frequency response which allows for the reception of signals f0 and f1 without additional trimming and complexity; is able to quickly transition between logic states to enable high-speed, high-bandwidth data transfer; and is respectful of power consumption and/or can increase the operating distance between the external controller and the IPG. This disclosure provides embodiments of such a solution.

BRIEF DESCRIPTION OF THE DRAWINGS

FIG. 2 shows the relation between the IPG of FIG. 1 and an external controller with which it communicates via magnetic inductive coupling.

DETAILED DESCRIPTION

The description that follows relates to use of the invention within a spinal cord stimulation (SCS) system. However, it is to be understood that the invention is not so limited. Rather, the invention may be used with any type of implantable medical device system that could benefit from improved communications between an external controller and the device. For example, the present invention may be used as part of a system employing an implantable sensor, an implantable pump, a pacemaker, a defibrillator, a cochlear stimulator, a retinal stimulator, a stimulator configured to produce coordinated limb movement, a cortical and deep brain stimulator, or in any other neural stimulator configured to treat any of a variety of conditions.

Figure 5:
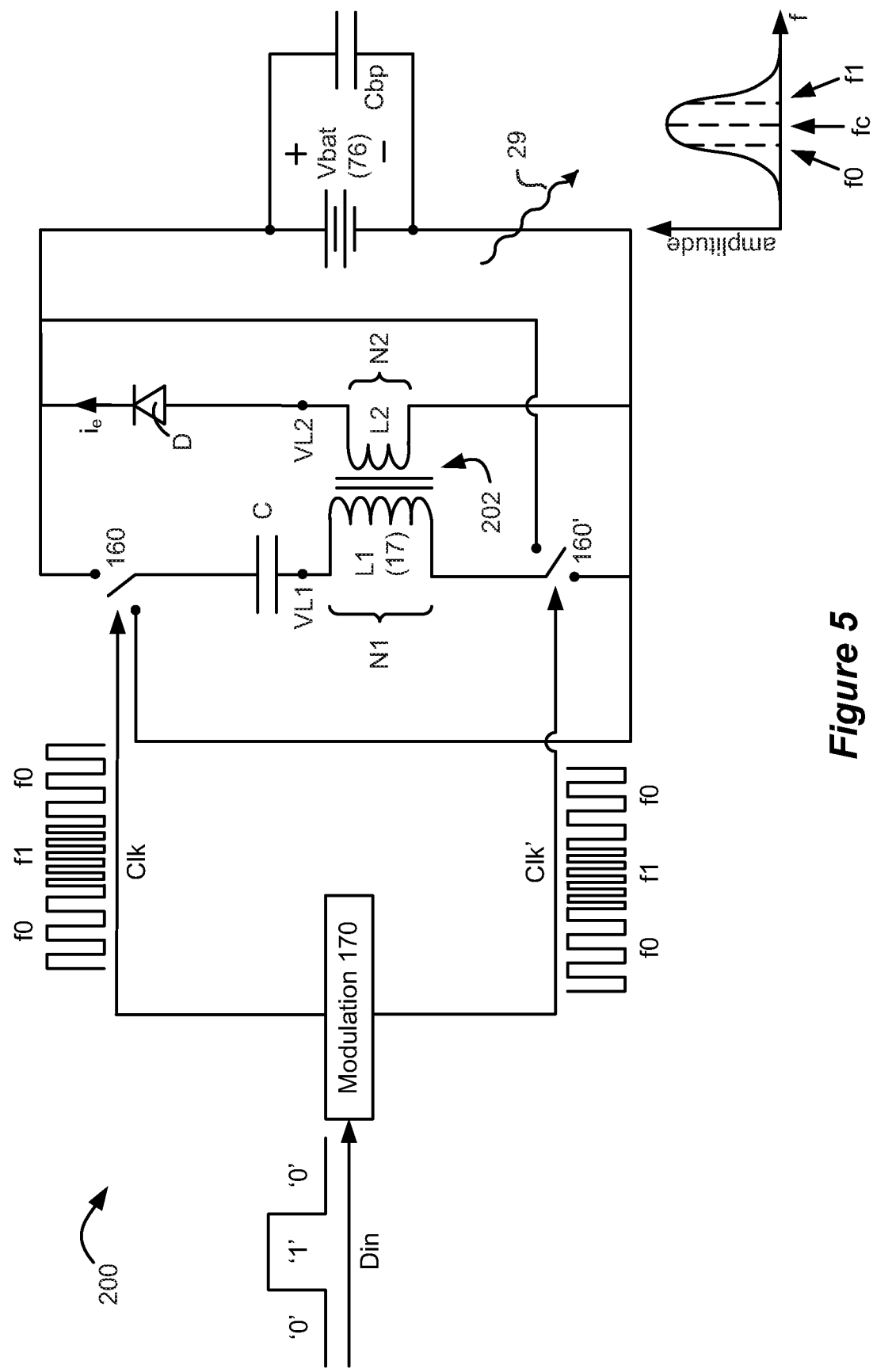
FIGS. 5 and 6 show embodiments of an improved driving circuit in accordance with the invention.

One embodiment of the improved driving circuit 200 is shown in FIG. 5, which offers significant improvement in power efficiency while at the same time being easy to implement. As will be discussed further below, the driving circuit 200 allows some of the excess current produced during resonance of the coil L to be shunted back to the rechargeable battery in the transmitter (e.g., the external controller). In so doing, the driving circuit 200 is naturally dampened, but in a way that is considerate of battery capacity. The result is a driving circuit which has a relatively broad frequency response profile. This allows frequencies f0 and f1 to be adjusted by the transmitter to match receiver characteristics without using additional circuits or hardware; is relatively responsive to allow for fast transitions between logic states and fast data rates; and is energy efficient.

Figures 1A, 1B:
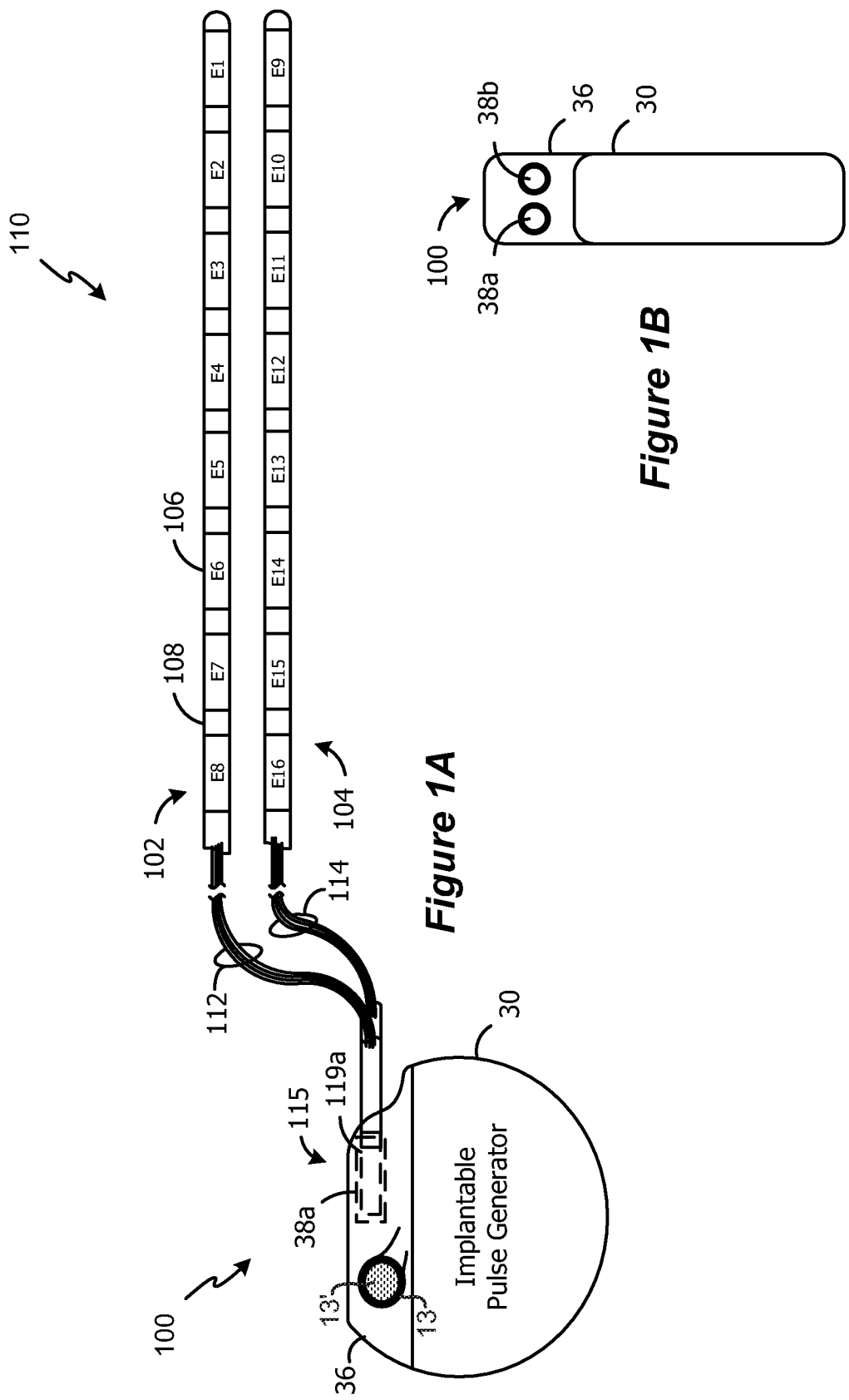
FIGS. 1A and 1B show an implantable pulse generator (IPG), and the manner in which an electrode array is coupled to the IPG in accordance with the prior art.
Figure 3:
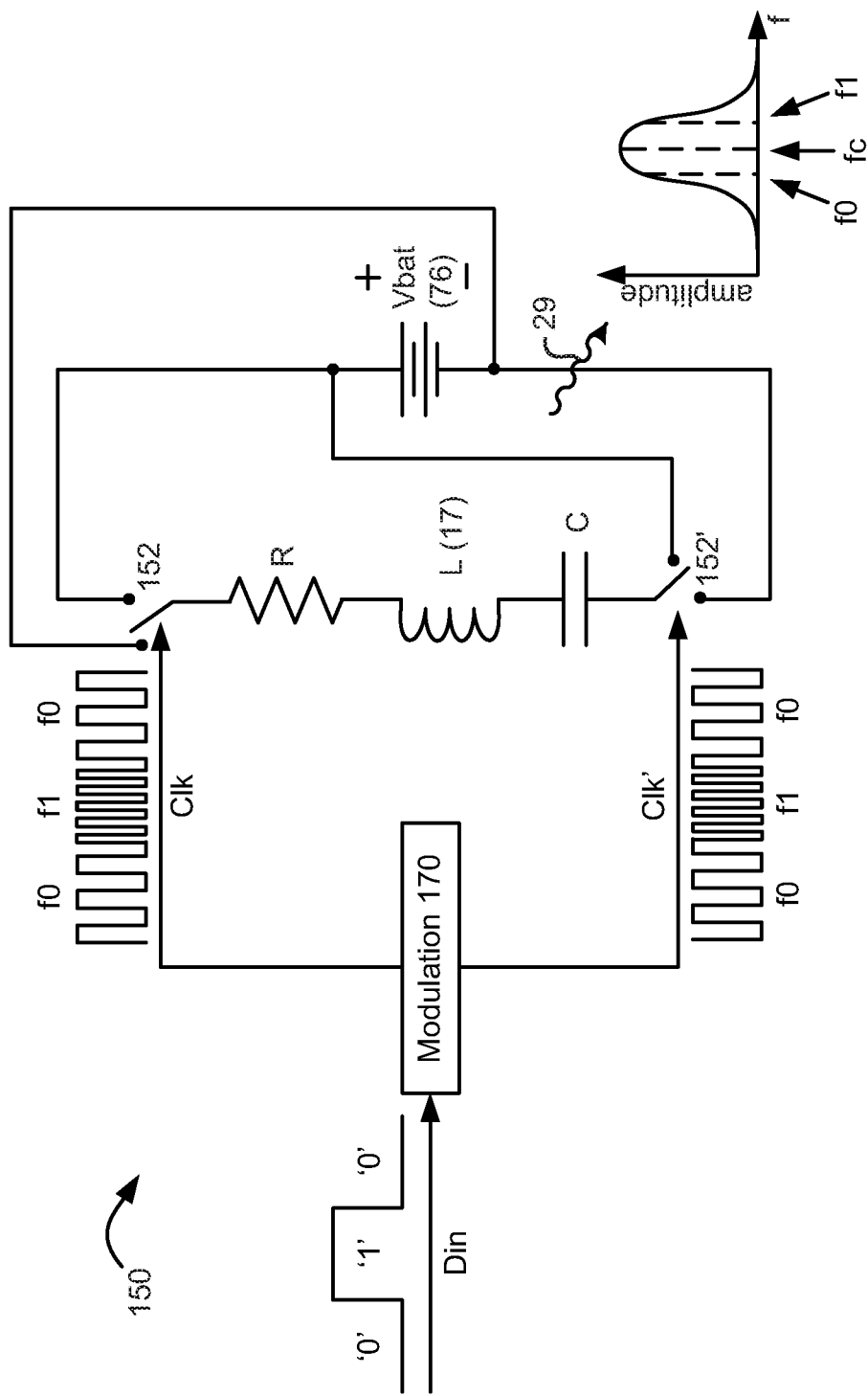
FIGS. 3 and 4 show prior art driving circuits for driving a coil to produce wireless data signals via magnetic inductive coupling.

The driving circuit 200 of FIG. 5 uses a transformer 202 with a primary winding L1 (which comprises the coil 17 in the external controller 12 for example) and a secondary winding L2 in a transformer feedback configuration. As shown, no discrete resistors (such as used in the approach of FIG. 3) are used in the resonant circuit, which comprises the resonance capacitor, C and the equivalent inductance L of the primary coil of the transformer 202. The circuit 200 produces a center resonance frequency, fc, in a medical implantable system application of about 125 kHz, where fc=$(2\pi*sqrt(LC))^{-1}$.

The primary winding L1(17) in conjunction with capacitor C, are made to resonate by toggling switches 160 and 160'. Because the switches 160 and 160' are controlled with complementary clock signals, Clk and Clk', Vbat is applied to the resonant circuit with alternating polarities. Driving the resonant circuit from both of its ends by the two switches 160 and 160' has the benefit of doubling the voltage across coil L1 and thus doubling magnetic field 29. However, the use of two switches 160 and 160' is not strictly necessary, and instead a single switch can be used in driving circuit as well (such as will be illustrated in the alternative embodiment of FIG. 6 below).

The windings or coils L1 and L2 in the transformer 202 have N1 and N2 turns respectively, which set the relation of the voltages across them: VL1=VL2*N1/N2. The voltage produced on the secondary winding L2, VL2, is connected to the battery 76 via a diode D. This has the effect of limiting VL2 to the battery voltage, Vbat. (This assumes that the threshold voltage of the diode is negligible, i.e., Vt≈0). Should VL2 try to exceed Vbat during resonance, the diode D becomes forward biased (again, assuming that the diode has a threshold voltage of zero, i.e., Vt≈0), and a battery recovery current, $i_e$, flows to the battery 76. Such current flow limits the potential of VL2 to Vbat, which in turn clamps the voltage across the coil 17 L1 to a maximum value: VL1max=Vbat*(N1/N2). (Should a significant diode threshold voltage Vt be present, this equation is modified as follows: VL1max=(Vbat+Vt)*(N1/N2)). By contrast, when VL2 is less than Vbat during resonance, the diode D prevents the flow of current out of the battery 76 ($i_e$≈0) to prevent discharging. The bypass capacitor Cbp reduces the peak current flowing in/out of the rechargeable battery 76 to provide for stability.

Figure 4:
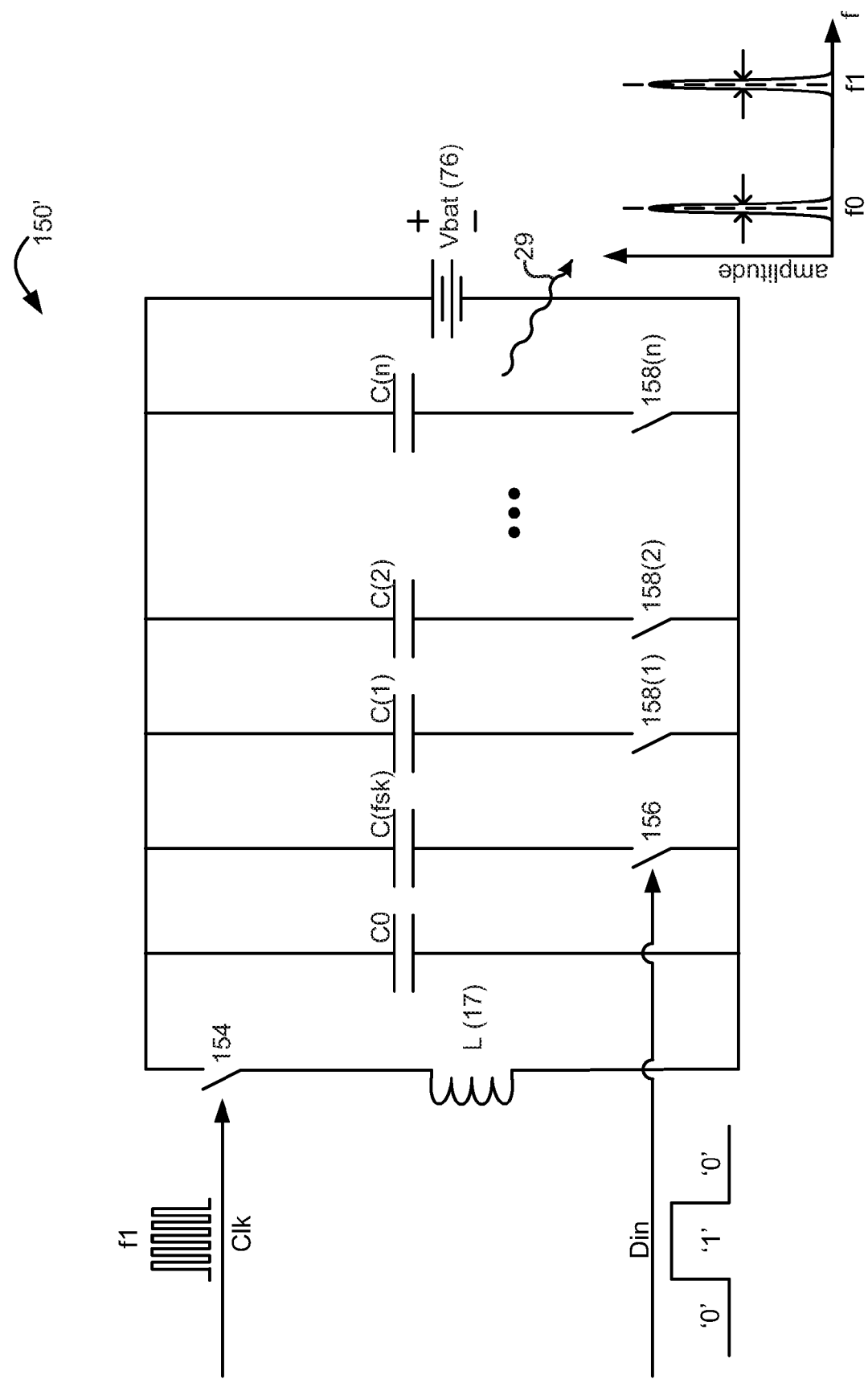

By shunting the recovery current $i_e$ to the rechargeable battery 76, the battery 76 is recharged. Such recharging occurs during a portion of the time that the circuit is resonating, i.e., when the resonance produces high voltages across the coil 17 that (absent clamping) would exceed Vbat*(N1/N2). The result is an energy efficient solution rivaling that of the solution depicted in FIG. 4. This is not without its drawbacks: because VL1 is clamped to VL1max, the magnetic field of the wireless modulated data signal 29 produced by the coil 17 is also limited, and thus the driving circuit 200 effectively acts as a low-Q-factor circuit. However, and unlike the solution of FIG. 3, such magnetic field reduction does not result from energy dissipation caused through the use of a discrete resistor.

Moreover, shunting the recovery current $i_e$ assists in dampening the resonance, which allows the driving circuit 200 to switch frequencies, and hence data states, more quickly, enabling the transmission of higher data rates. Such active dampening also tends to spread the width of the resonance of the driving circuit (i.e., at 121 kHz and 129 kHz). This eases the need to precisely match hardware components of the driving circuit 200 to that of the receiver, and hence allows the driving circuit to be constructed of components of lesser accuracy.

The various values for the components used in the improved driving circuit 200 of FIG. 5 may be as follows for the medical implantable device system for which the circuit was originally developed. N1=~22 turns; N2=~3 turns; L1=34 µH; C=0.047 µF; Vbat=4.1V; Cbp=100 µF. However, in a different application, different component values could be chosen.

Figure 6:
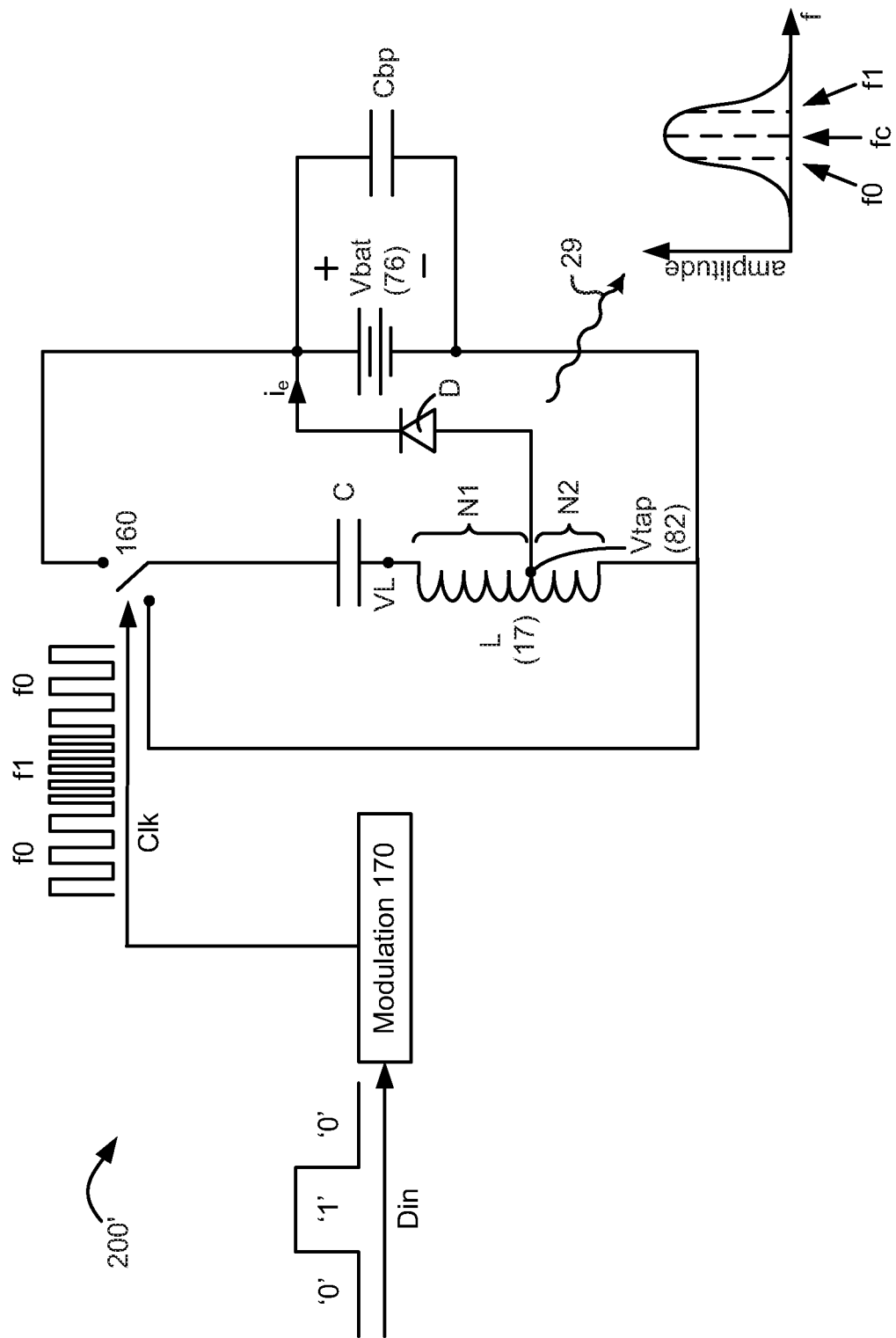

FIG. 6 depicts an alternative driving circuit 200'. Like the driving circuit 200 of FIG. 5, the driving circuit 200' of FIG. 6 also lacks a discrete resistor, but also allows for excess resonance energy to be shunted back to the battery 76 for the purpose of dampening and recharging. Driving circuit 200' employs a single inductor L (i.e., the coil of the external controller 12 for example). A tap point 82 is added to the transmit coil 17 (in what is known in the art as an autotransformer configuration) to connect the coil 17 to the rechargeable battery 76 via a diode, D. The number of turns in the coil above (N1) and below (N2) the tap point 82 relates the voltage across the coil (VL) to the voltage at the tap point 82 (Vtap). Specifically, VL=Vtap*(N2+N1)/N2.

As in the transformer feedback configuration of FIG. 5, the diode D has the effect of clamping the voltage across the coil 17 to a maximum, VLmax. This is because the voltage at tap point 82 (Vtap) cannot exceed the battery voltage (Vbat). Should Vtap try to exceed Vbat during resonance, the diode D becomes forward biased (assuming that the diode has a threshold voltage of zero, i.e., Vt≈0), and a battery recovery current, $i_e$, flows to the battery 76. Such current flow limits the potential of Vtap to Vbat, which in turn clamps the voltage across the coil 17 to a maximum value: VLmax=Vbat*(N2+N1)/N2. (Should a significant diode threshold voltage Vt be present, this equation is modified as follows: VLmax=(Vbat+Vt)*(N2+N1)/N2). By contrast, when Vtap is less than Vbat during resonance, the diode D prevents the flow of current out of the battery 76 ($i_e$≈0) to prevent discharging. As with the driving circuit 200 of FIG. 5, the center frequency of resonance is fc=$(2\pi*sqrt(LC))^{-1}$, where L comprises the inductance of the coil L 17.

The effect, as with the driving circuit 200 of FIG. 5, is that recovery current $i_e$ is shunted to the rechargeable battery 76 during high voltage portions of the resonance, providing a very energy efficient solution. Although VL is clamped to VLmax, which limits the magnetic field producible by the coil 17, such magnetic field reduction does not result from energy dissipation caused through the use of a discrete resistor. And once again, shunting the recovery current $i_e$ to the battery assists in dampening the resonance, which allows for the transmission of higher data rates. Additionally, and as before, such active dampening also tends to widen the resonant response of the resonant circuit, easing reception without the need for hardware trimming.

The various values for the components used in the improved driving circuit 200' of FIG. 6 may be as follows for the medical implantable device system for which the circuit was originally developed. N1=~20 turns; N2=~4 turns; L=34 µH; C=0.047 µF; Vbat=4.1V; Cbp=100 µF. However, in a different application, different component values could be chosen.

The disclosed driving circuits can be used with any switching type amplifier (Class C, D, E, H, etc.), and for both the transformer feedback configuration (FIG. 5) and the autotransformer (FIG. 6) configuration.

While disclosed in the context of a medical implantable device system for which the invention was originally contemplated, it should be recognized that the improved driving circuitry disclosed herein is not so limited, and can be used in other contexts employing communications via magnetic inductive coupling, such as in Radio-Frequency Identification (RFID) systems, etc. The disclosed circuitry can further be used in any context in which magnetic inductive coupling could be used as a means of communication, even if not so used before.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A driving circuit useful in a magnetic inductive coupling wireless communication system, comprising:
    a rechargeable battery having a battery voltage;
    a resonant circuit including a coil;
    at least one switch for selectively connecting the battery voltage to the resonant circuit, wherein the switch is operated by a modulated data signal;
    a node comprising a tap into a portion of the coil; and
    a diode interposed between the tap and the rechargeable battery,
    wherein the diode shunts current to the rechargeable battery.

2. The circuit of claim 1, wherein the modulated data signal comprises two frequencies corresponding to two logic states.

3. The circuit of claim 1, wherein the diode functions to clamp a voltage across the coil to a maximum voltage.

4. The circuit of claim 1, wherein the resonant circuit comprises a capacitor in series with the coil.

5. The circuit of claim 1, wherein the resonant circuit does not include a discrete resistor.

6. The circuit of claim 1, further comprising a bypass capacitor in parallel with the rechargeable battery.

* * * * *